US00PP10582P

United States Patent [19]

Bergman

[11] Patent Number: Plant 10,582

[45] Date of Patent: Sep. 1, 1998

[54] HIBISCUS PLANT NAMED 'BIMINI BREEZE'

[75] Inventor: Wendy R. Bergman, Lehigh Acres, Fla.

[73] Assignee: Yoder Brothers, Inc., Barberton, Ohio

[21] Appl. No.: 807,403

[22] Filed: Feb. 27, 1997

[51] Int. Cl.[6] ..... A01H 5/00

[52] U.S. Cl. ..... Plt./67.8

[58] Field of Search ..... Plt./67.8

*Primary Examiner*—James R. Feyrer

*Attorney, Agent, or Firm*—C. A. Whealy

[57] ABSTRACT

A new and distinct cultivar of Hibiscus plant named 'Bimini Breeze', characterized by its very dark green leaves; upright and outwardly spreading, uniform and symmetrical plant habit; numerous bright pink-colored flowers with dark red throats; good resistance to flower bud abscission; and excellent postproduction longevity.

3 Drawing Sheets

The present invention relates to a new and distinct cultivar of Hibiscus, botanically known as *Hibiscus rosa-sinensis*, and hereinafter referred to by the cultivar name 'Bimini Breeze'.

The new cultivar is a product of a planned breeding program conducted by the inventor in Alva, Fla. The objective of the breeding program is to create new Hibiscus cultivars having uniform plant habit, early flowering, numerous flowers per lateral branch, desirable flower color, resistance to flower bud abscission, and good postproduction longevity.

The new cultivar originated from a cross made by the inventor in Alva, Fla. of the commercial cultivar 'Waikiki' (disclosed in U.S. Plant Pat. No. 7,834) as the female, or seed, parent with the nonpatented commercial cultivar 'Pink Versicolor' as the male, or pollen, parent. Compared to plants of the cultivar 'Waikiki', plants of the new Hibiscus have a more uniform and compact plant habit, darker green foliage, smaller flowers, and more uniform bud development. Compared to plants of the cultivar 'Pink Versicolor', plants of the new Hibiscus have darker and smaller leaves, smaller flowers, and more intense pink-colored flowers.

The cultivar 'Bimini Breeze' was discovered and selected by the inventor as a flowering plant within the progeny of the stated cross in a controlled environment in Alva, Fla., on Oct. 1, 1993. The selection of this plant was based on its desirable flower color, resistance to flower bud abscission, good postproduction longevity, and uniform plant habit and flowering.

Asexual reproduction of the new cultivar by terminal cuttings taken in a controlled environment in Alva, Fla., has shown that the unique features of this new Hibiscus are stable and reproduced true to type in successive generations.

The cultivar 'Bimini Breeze' has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Bimini Breeze'. These characteristics in combination distinguish 'Bimini Breeze' as a new and distinct cultivar:

1. Very dark green leaves.
2. Upright and outwardly spreading, uniform and symmetrical plant habit.
3. Numerous bright pink-colored flowers with dark red throats.
4. Good resistance to flower bud abscission.
5. Excellent postproduction longevity.

The accompanying colored photographs illustrate the overall appearance of the new cultivar, showing the colors as true as it is reasonably possible to obtain in colored reproductions of this type.

The first photograph comprises a side perspective view of typical plant of 'Bimini Breeze'.

The second photograph comprises a close-up view of a typical flower of 'Bimini Breeze'.

The third photograph comprises a close-up view of typical flowers of 'Waikiki', left, and 'Bimini Breeze', right.

Flower and foliage colors in the photographs may appear different from the actual colors due to light reflectance.

The aforementioned and following observations, measurements, values, and comparisons describe plants grown in Alva, Fla., 15-cm containers with day temperatures ranging from 16° to 35° C. and night temperatures ranging from 10° to 24° C. Plants were grown under a polypropylene covering with light levels ranging from 6,000 to 9,000 footcandles.

In the following description, color references are made to The Royal Horticultural Society Colour Chart except where general terms of ordinary dictionary significance are used.

Botanical classification: *Hibiscus rosa-sinensis* cv. 'Bimini Breeze'.

Parentage:

*Male or pollen parent.*—*Hibiscus rosa-sinensis* cv. 'Pink Versicolor' (not patented).

*Female or seed parent.*—*Hibiscus rosa-sinensis* cv. 'Waikiki' (U.S. Plant Pat No. 7,834).

Propagation:

*Type.*—By terminal cuttings.

*Time to develop roots.*—About 28 days at temperatures of 24° C.

*Rooting habit.*—Moderately vigorous, thick and well-branched.

Plant description:

*Plant form and growth habit.*—Perennial, evergreen, upright and outwardly spreading, inverted triangle, uniform and symmetrical plant habit. Moderate vigor.

*Branching habit.*—Moderate to freely branching, usually three to four lateral branches develop after removal of terminal apex.

*Plant height, soil level to top of flowers.*—About 25 cm.

*Plant diameter, area of spread.*—About 40 cm.

*Lateral branch description.*—Length: About 6 cm. Diameter: About 5 mm. Color: Immature: 200A/

187A with green, 147A, overtones. Mature: Dark green, 147A, with gray, 197A.

Foliage description:

*Arrangement.*—Alternate, single.

*Leaf size, largest leaves.*—Length: About 10 cm. Width: About 7 cm.

*Leaf shape.*—Ovate.

*Leaf apex.*—Cuspidate.

*Leaf base.*—Obtuse.

*Margin type.*—Crenate.

*Texture.*—Glabrous and glossy on both surfaces.

*Aspect.*—Slightly undulating.

*Color.*—Young foliage, upper surface: Greener than 147A. Young foliage, lower surface: 146A. Mature foliage, upper surface: Very dark green, much darker than 147A. Mature foliage, lower surface: Lighter than 147A. Venation, upper surface: 147A. Venation, lower surface: 147A, midvein is greenish red.

*Petiole.*—Length: About 3 cm. Diameter: About 3 mm. Texture: Pubescence on abaxial surface. Color: 200A.

Flower description:

*Natural flowering season.*—Usually spring and summer or during periods of warm weather.

*Flower arrangement.*—Flowers arranged singly at terminal leaf axils. Freely flowering with usually four to six flower buds and/or open flowers per terminal apex. Flowers face upright.

*Flower appearance.*—Star-shaped single. Bright pink-colored petals with dark red throat. Flowers are open for about one day before closing. Flowers persistent.

*Flower diameter.*—About 14 cm.

*Flower bud (just before opening).*—Rate of opening: About one day depending on temperatures. Length: About 7 cm. Diameter: About 1.4 cm. Shape: Columnar. Color: Apex: 52B. Base: White.

*Petals.*—Texture: Satiny, smooth. Arrangement: Corolla consists of five petals that overlap. Shape: Spatulate with rounded apex. Margin: Entire. Size: Length: About 9 cm. Width: About 6.5 cm. Color: Upper surface: Bright pink, 52D at margin, darker pink, 55A, towards base. White where petals overlap. Veins are darker pink, 55A. Lower surface: Light pink, 55C, white at base and where petals overlap. Throat: Dark red, 53A/53B. After closing: Bright pink, 52D, white at base.

*Sepals.*—Appearance: Six sepals fused into a star-shaped calyx. Shape: Linear. Texture: Smooth. Color, outer surface: Greener than 146A.

*Peduncles.*—Length: About 3 cm. Diameter: About 3 mm. Angle: Upright. Strength: Strong, rigid. Color: 200B.

*Reproductive organs.*—Androecium: Stamen number: Numerous. Stamen length: About 5 mm. Anther shape: Globular. Anther size: About 1 mm. Amount of pollen: Abundant. Pollen color: 21A. Gynoecium: Pistil length: About 9.5 cm. Style length: About 7.5 cm. Style color: Apex: 19C. Base: 53B. Stigma shape: Round. Stigma diameter: About 2.5 mm. Stigma color: 45B. Ovary color: White.

Disease resistance: No known Hibiscus diseases observed to date on plants grown under commercial greenhouse conditions.

Seed production: If cross-pollinated, seed production may be observed. Usually one to twenty seeds per capsule.

It is claimed:

1. A new and distinct Hibiscus plant named 'Bimini Breeze', as illustrated and described.

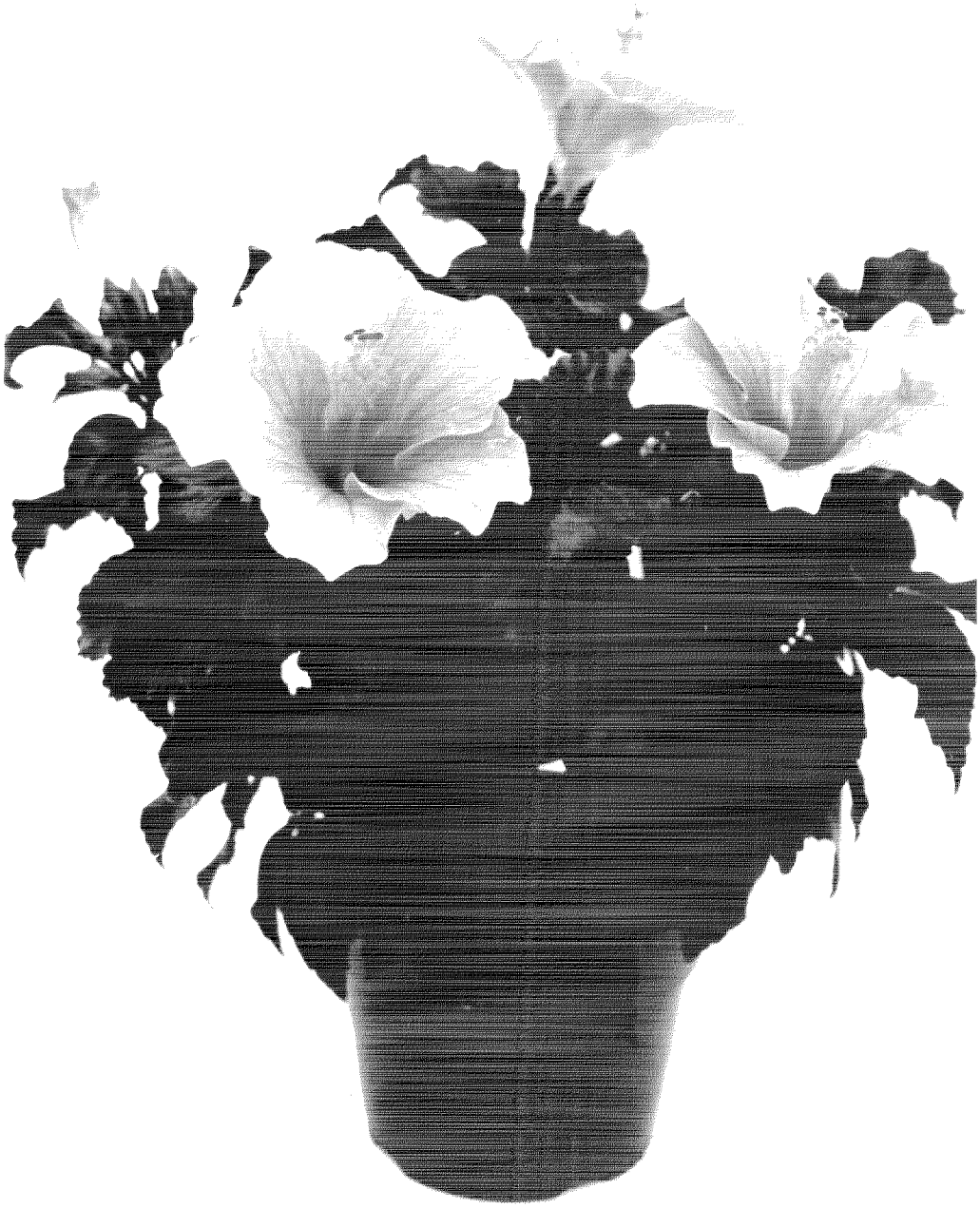

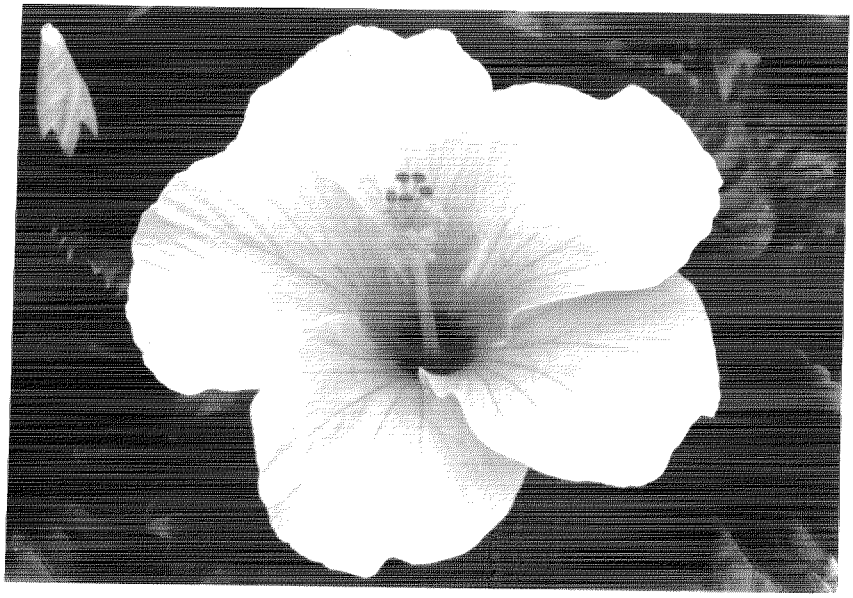

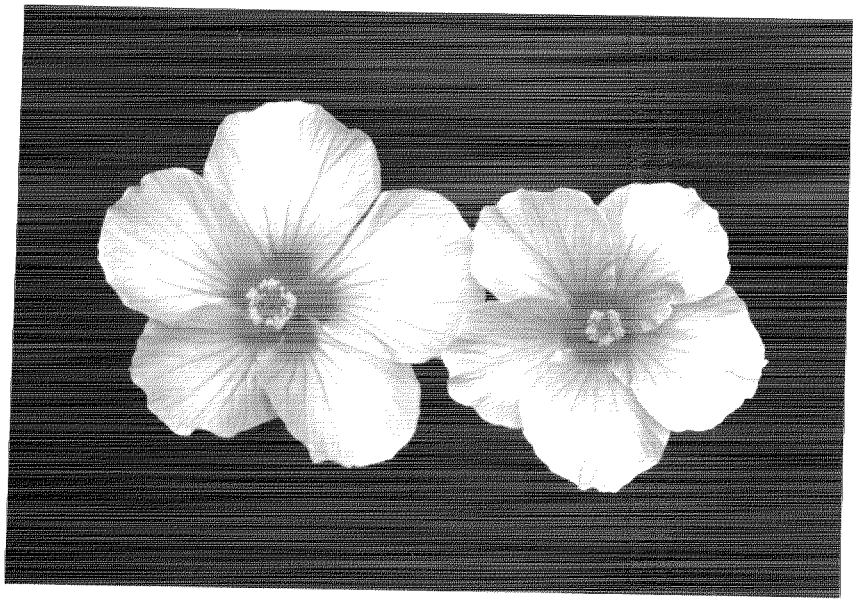

* * * * *